United States Patent
Feler et al.

(10) Patent No.: US 7,979,131 B2
(45) Date of Patent: Jul. 12, 2011

(54) METHOD OF NEUROSTIMULATION OF DISTINCT NEURAL STRUCTURES USING SINGLE PADDLE LEAD TO TREAT MULTIPLE PAIN LOCATIONS AND MULTI-COLUMN, MULTI-ROW PADDLE LEAD FOR SUCH NEUROSTIMULATION

(75) Inventors: Claudio A. Feler, Memphis, TN (US); John H. Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 355 days.

(21) Appl. No.: 11/627,699

(22) Filed: Jan. 26, 2007

(65) Prior Publication Data

US 2007/0179579 A1      Aug. 2, 2007

Related U.S. Application Data

(60) Provisional application No. 60/762,616, filed on Jan. 26, 2006.

(51) Int. Cl.
*A61N 1/34* (2006.01)

(52) U.S. Cl. .......................................... 607/46; 607/117

(58) Field of Classification Search .................... 607/46, 607/117
See application file for complete search history.

(56) References Cited

U.S. PATENT DOCUMENTS

| | | | |
|---|---|---|---|
| 5,643,330 A | | 7/1997 | Holsheimer et al. |
| 5,895,416 A | | 4/1999 | Barreras, Sr. et al. |
| 6,038,480 A | * | 3/2000 | Hrdlicka et al. ............. 607/116 |
| 6,236,892 B1 | | 5/2001 | Feler |
| 6,438,423 B1 | * | 8/2002 | Rezai et al. ...................... 607/46 |
| 6,505,078 B1 | * | 1/2003 | King et al. ...................... 607/67 |
| 6,754,539 B1 | * | 6/2004 | Erickson et al. .............. 607/117 |
| 6,871,099 B1 | * | 3/2005 | Whitehurst et al. ............ 607/46 |
| 6,978,180 B2 | | 12/2005 | Tadlock |
| 7,072,719 B2 | | 7/2006 | Vinup et al. |
| 7,590,454 B2 | | 9/2009 | Garabedian et al. |
| 2002/0128694 A1 | | 9/2002 | Holsheimer |

(Continued)

OTHER PUBLICATIONS

Bennett, et al., "Spinal Cord Stimulation for Complex Regional Pain Syndrome I [RSD]: a Retrospective Multicenter Experience from 1995 to 1998 of 101 Patients," Neuromodulation 2(3): 202-210 (1999), p. 203, col. 2, ln 19-27; p. 204, Fig. 2, p. 208, col. 2, para 2.

(Continued)

*Primary Examiner* — Michael Kahelin
(74) *Attorney, Agent, or Firm* — Melissa Acosta; Christopher S. L. Crawford; Craig Hoersten

(57) ABSTRACT

In some embodiments, a paddle lead is implanted within a patient such that the electrodes are positioned within the cervical or thoracic spinal levels. An electrode combination on a first row of electrodes can be determined that is effective for a first pain location with minimal effects on other regions of the body. The first pain location can be addressed by stimulating a first dorsal column fiber due to the relatively fine electrical field resolution achievable by the multiple columns. Then, another electrode combination on a second row of electrodes can be determined for a second pain location with minimal effects on other regions. The second pain location could be addressed by stimulating a second dorsal column fiber. After the determination of the appropriate electrodes for stimulation, the patient's IPG can be programmed to deliver pulses using the first and second rows according to the determined electrode combinations.

7 Claims, 6 Drawing Sheets

U.S. PATENT DOCUMENTS

| | | |
|---|---|---|
| 2004/0210291 A1 | 10/2004 | Erickson et al. |
| 2005/0070982 A1 | 3/2005 | Heruth et al. |
| 2005/0700982 | 3/2005 | Heruth et al. |
| 2006/0253182 A1 | 11/2006 | King |
| 2007/0027514 A1 | 2/2007 | Gerber |
| 2007/0027515 A1 | 2/2007 | Gerber |

OTHER PUBLICATIONS

Johannes J. Struijk, et al.; "*Theoretical Performance and Clinical Evaluation of Transverse Tripolar Spinal Cord Stimulation*," IEEE Transactions on Rehabilitation Engineering, vol. 6, No. 3, Sep. 1998.

Jan Holsheimer, et al., "*Clinical Evaluation of Paresthesia Steering with a New System for Spinal Cord Stimulation*," Neurosurgery, vol. 42, No. 3, Mar. 1998.

K. E. I. Deurloo, et al., "*Transverse tripolar stimulation of peripheral nerve: a modelling study of spatial selectivity*," Med. Biol. Eng. Comput., 1998, 36, 66-74.

Feirabend, H.K.P., et al., "Morphometry of human superficial dorsal and dorsolateral column fibres: significance to spinal cord stimulation," Brain, 2002, 125, 1137-1149.

Murphy, Donald R., et al., "Pain patterns and descriptions in patients with radicular pain: Does the pain necessarily follow a specific dermatome?," Chiropractic & Osteopathy, 2009, 17:0, 1-9.

Oakley, John C., MD, et al., "Transverse Tripolar Spinal Cord Stimulation: Results of an International Multicenter Study," Neuromodulation, 2006, vol. 9, No. 3, 192-203.

Smith, Marion C., et al., Topographical anatomy of the posterior columns of the spinal cord in man, Brain, 1984, 107, 671-698.

Struijk, J.J., et al., "Transverse tripolar spinal cord stimulation: theoretical performance of a dual channel system," Med. & Biol. Eng. & Comput., 1996, 34, 273-279.

Wesselink, Wilbert A., PhD., et al., "Quantitative aspects of the clinical performance of transverse tripolar spinal cord stimulation," Neuromodulation, vol. 2, No. 1, 1999, 5-14.

\* cited by examiner

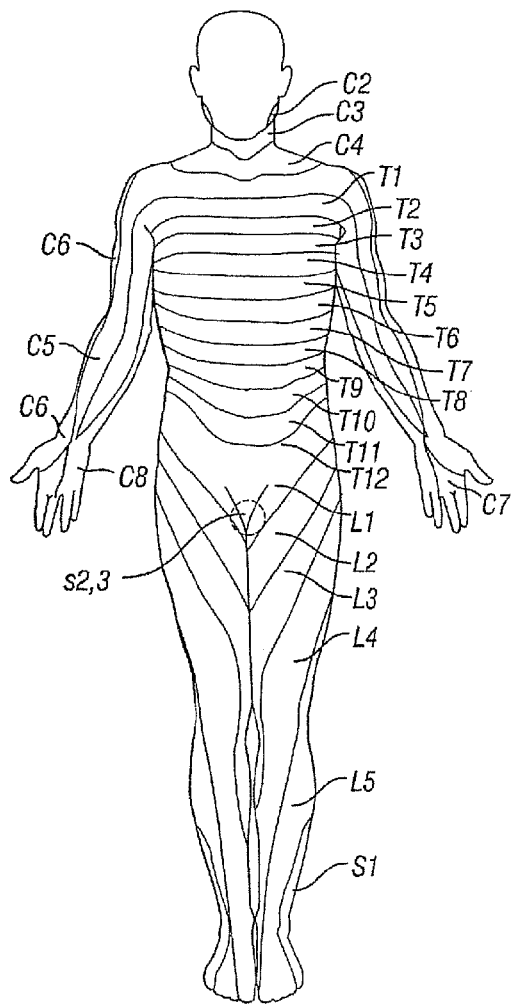
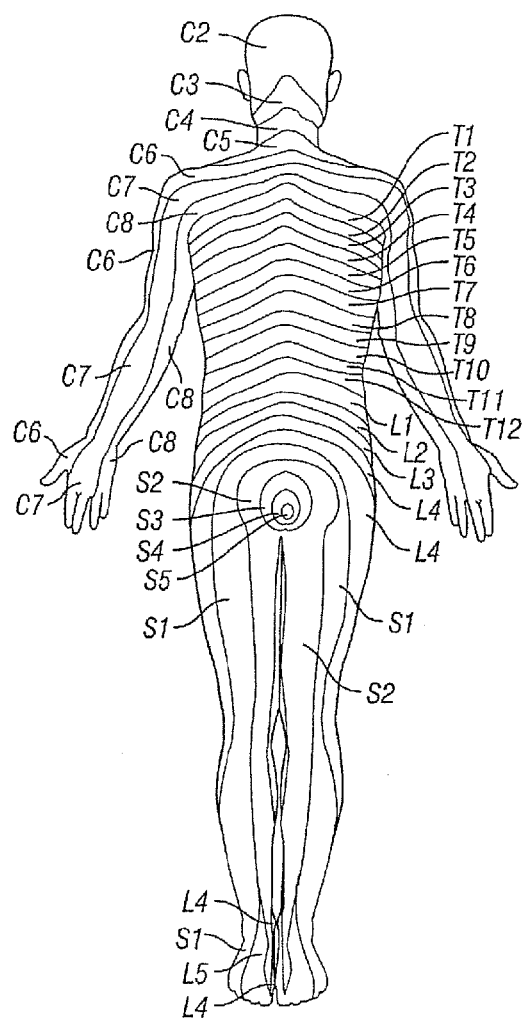
FIG. 4A
FIG. 4B

METHOD OF NEUROSTIMULATION OF DISTINCT NEURAL STRUCTURES USING SINGLE PADDLE LEAD TO TREAT MULTIPLE PAIN LOCATIONS AND MULTI-COLUMN, MULTI-ROW PADDLE LEAD FOR SUCH NEUROSTIMULATION

RELATED APPLICATION

The present application claims the benefit of Provisional Patent Application Ser. No. 60/762,616, filed Jan. 26, 2006, entitled "METHOD OF NEUROSTIMULATION OF DISTINCT NEURAL STRUCTURES USING SINGLE PADDLE LEAD TO TREAT MULTIPLE PAIN LOCATIONS AND MULTI-COLUMN, MULTI-ROW PADDLE LEAD FOR SUCH NEUROSTIMULATION," which is incorporated herein by reference.

TECHNICAL FIELD

The present application is generally related to providing an effective neuromodulation therapy for multiple pain locations using a multi-column, multi-row paddle lead.

BACKGROUND

Application of electrical fields to spinal nerve roots, spinal cord, and other nerve bundles for the purpose of chronic pain control has been actively practiced for some time. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Each exterior region, or each dermatome, of the human body is associated with a particular spinal nerve root at a particular longitudinal spinal position. The head and neck regions are associated with C2-C8, the back regions extends from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. By example, to address chronic pain sensations that commonly focus on the lower back and lower extremities using conventional techniques, a specific energy field is typically applied to a region between vertebrae levels T8 and T12. The specific energy field often stimulates a number of nerve fibers and structures of the spinal cord. By applying energy in this manner, the patient commonly experiences paresthesia over a relatively wide region of the patient's body from the lower back to the lower extremities.

Positioning of an applied electrical field relative to a physiological midline is also important. Nerve fibers extend between the brain and a nerve root along the same side of the dorsal column as the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral." Accordingly, bilateral pain is addressed through application of electrical energy along both sides of the column and/or along a patient's physiological midline.

Percutaneous leads and laminotomy leads are the two most common types of lead designs that provide conductors to deliver stimulation pulses from an implantable pulse generator (IPG) to distal electrodes adjacent to the pertinent nerve tissue. As shown in FIG. 1A, conventional percutaneous lead 100 includes electrodes 101 that substantially conform to the body of the body portion of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

As shown in FIG. 1B, conventional laminotomy or paddle lead 150 has a paddle configuration and typically possesses a plurality of electrodes 151 (commonly, two, four, eight, or sixteen) arranged in columns. Due to their dimensions and physical characteristics, conventional laminotomy leads require a surgical procedure (a partial laminectomy) for implantation. Multi-column laminotomy leads enable more reliable positioning of a plurality of electrodes as compared to percutaneous leads. Also, laminotomy leads offer a more stable platform that tends to migrate less after implantation and that is capable of being sutured in place. Laminotomy leads also create a uni-directional electrical field and, hence, can be used in a more electrically efficient manner than typical percutaneous leads.

To supply suitable pain-managing electrical energy, multi-programmable IPGs enable the pattern of electrical pulses to be varied across the electrodes of a lead. Specifically, such systems enable electrodes of a connected stimulation lead to be set as an anode (+), as a cathode (−), or to a high-impendence state (OFF). As is well known, negatively charged ions and free electrons flow away from a cathode toward an anode. Consequently, using laminotomy lead 150 of FIG. 1B as an example, a range of very simple to very complex electrical fields can be created by defining different electrodes in various combinations of (+), (−), and OFF. Of course, in any instance, a functional combination must include at least one anode and at least one cathode (although in some cases, the "can" of the IPG can function as an anode).

SUMMARY

In some embodiments, a paddle lead is provided with multiple columns and multiple rows. The paddle lead is preferably implanted within a patient such that the electrodes are positioned within the cervical or thoracic spinal levels. After implantation, an electrode combination on a first row of electrodes can be determined that is effective for a first pain location with minimal effects on other regions of the body. The first pain location can be addressed by stimulating a first dorsal column fiber due to the relatively fine electrical field resolution achievable by the multiple columns. Then, another electrode combination on a second row of electrodes can be determined for a second pain location with minimal effects on other regions of the body. The second pain location could be addressed by stimulating a second dorsal column fiber. After the determination of the appropriate electrodes for stimulation, the patient's IPG can be programmed to deliver pulses using the first and second rows according to the determined electrode combinations. By employing such a stimulation methodology, relatively complex pain patterns can be addressed while only requiring a single implantation.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 4A and 4B depict the dermatomes areas.

DETAILED DESCRIPTION

I. Definitions

Figure 1A:
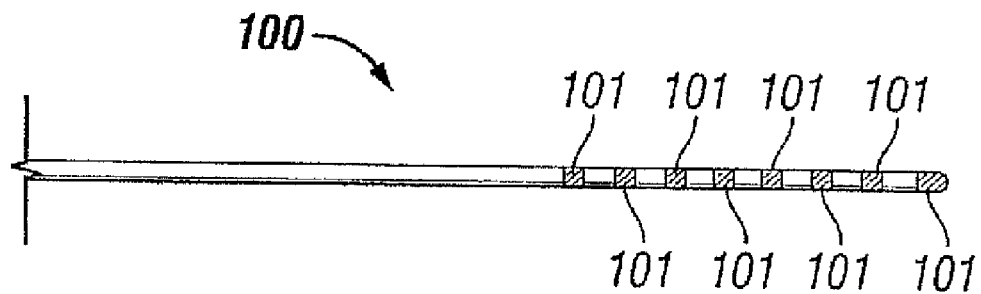
FIGS. 1A and 1B respectively depict conventional percutaneous and paddle leads.
Figure 1B:
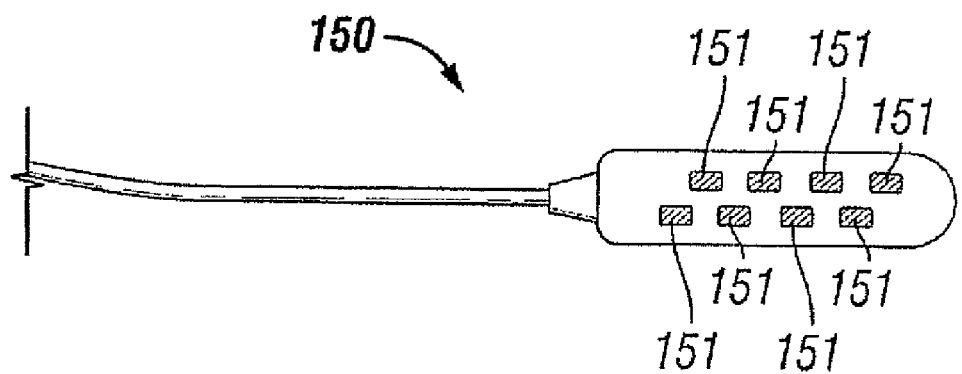

Unless defined otherwise, technical and scientific terms used herein have the same meaning as commonly understood by one of ordinary skill in the art to which this invention belongs. For purposes of the present application, the following terms are defined below.

As used herein, the use of the word "a" or "an" when used in conjunction with the term "comprising" in the claims and/ or the specification may mean "one", but it is also consistent with the meaning of "one or more," "at least one", and "one or more than one". Still further, the terms "having", "including", "containing" and "comprising" are interchangeable and one of skill in the art is cognizant that these terms are open-ended terms. Some embodiments of the invention may consist of or consist essentially of one or more elements, method steps, and/or methods of the invention. It is contemplated that any method or composition described herein can be implemented with respect to any other method or composition described herein.

As used herein, the use of the term "dorsal column" refers to conducting pathways in the spinal cord that are located in the dorsal portion of the spinal cord between the posterior horns, and which comprises afferent somatosensory neurons. The dorsal column is also known as the posterior funiculus.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

As used herein the term "chronic pain" refers to a persistent state of pain experienced for a substantial amount of time (e.g., longer than three months).

As used herein the term "complex regional pain syndrome" or "CRPS" refers to painful conditions that usually affect the distal part of an upper or lower extremity and are associated with characteristic clinical phenomena. CRPS is divided into two subtypes CRPS Type I and CRPS Type II. Generally, the clinical characteristics of Type I are the same as seen in Type II. The central difference between Type I and Type II is that Type II typically occurs following a sensory nerve injury whereas Type I occurs in the absence of any known nerve injury.

II. Organization of the Nervous System

The nervous system comprises two general components, the central nervous system, which is composed of the brain and the spinal cord, and the peripheral nervous system, which is composed of ganglia or dorsal root ganglia and the peripheral nerves that lie outside the brain and the spinal cord. One of skill in the art realizes that the nervous system may be linguistically separated and categorized, but functionally they are interconnected and interactive.

Figure 2:
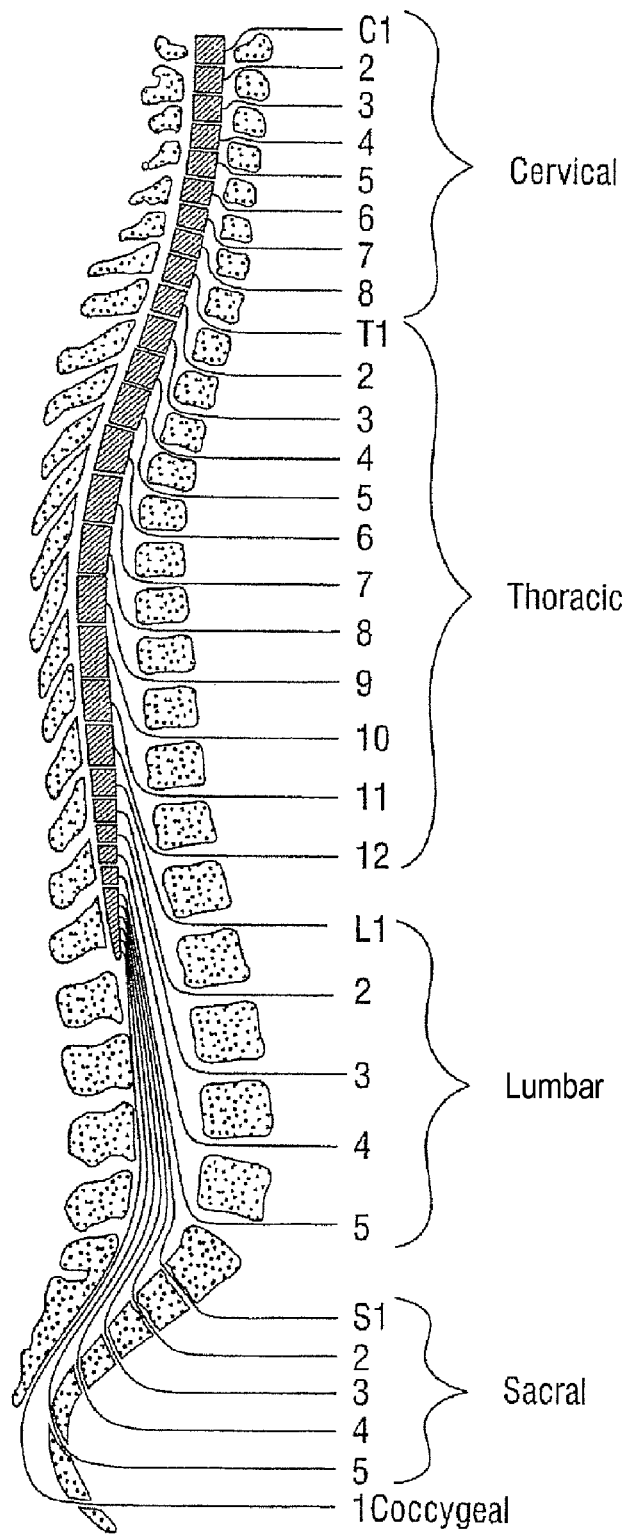
FIG. 2 depicts the spinal cord and the nerve roots in relation to the vertebral spinal canal.
Figure 3:
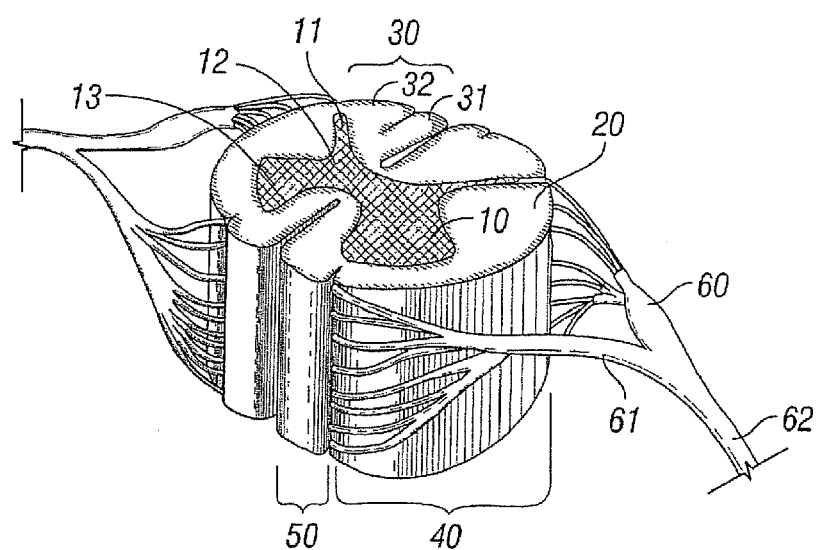
FIG. 3 depicts the anatomical structures of the spinal cord.

The central nervous system comprises the brain and spinal cord, which together function as the principal integrator of sensory input and motor output. In general terms, the brain consists of the cerebrum (cerebral hemispheres and the diencephalons), the brainstem (midbrain, pons, and medulla); and the cerebellum. The spinal cord is organized into segments, for example, there are 8 cervical (C1-C8), 12 thoracic (T1-T12), 5 lumbar (L1-L5), 5 sacral (S1-S5), and 1 cocygeal (Co1) spinal segments. In adults, the spinal cord typically ends at the level of the L1 or L2 vertebral bones. As shown in FIG. 2, the nerve roots travel downward to reach their exit points at the appropriate levels. Left and right sensory and motor nerve roots arise from each segment of the spinal cord except for the C1 and Co1 segments, which have no sensory roots. As shown in FIG. 3, the sensory nerve root 301 and motor nerve root 302 fuse to form a single mixed spinal nerve 303 for each segment. The mixed spinal nerves further fuse and intermingle peripherally to form plexuses and nerve branches.

The peripheral nervous system is divided into the autonomic system (parasympathetic and sympathetic), the somatic system and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

A. Organization of the Spinal Cord

The present application is drawn to specific stimulation of fibers in the spinal cord, thus, a further description of the spinal cord is discussed herein.

The spinal cord is known to contain a butterfly-shaped central gray matter surrounded by ascending and descending white matter columns or funiculi. Sensory neurons in the dorsal root ganglia have axons that bifurcate. One branch relays sensory information from the periphery and the other branch carries this information through the dorsal nerve root filaments into the dorsal aspect of the spinal cord. The peripheral region that is innervated by sensory fibers from a single nerve root is known as a dermatome. As shown in FIGS. 4A and 4B, dermatomes are divided into sacral (S1-S5), lumbar (L1-L5), thoracic (T1-T12) and cervical (C2-C8).

FIG. 3 shows that the central gray matter 10 of the spinal cord can be divided into the dorsal (posterior) horn 11 that is involved in sensory processing, an intermediate zone 12 that contains interneurons and specialized nuclei and a ventral (anterior) horn 13 that contains motor neurons. The white matter 20 of the spinal cord is divided into dorsal or posterior columns 30, lateral columns 40 and ventral or anterior columns 50. Those of skill in the art realize that the spinal cord does not appear the same at all levels; for example, the white matter is thickest in the cervical levels, where the most ascending fibers have already entered the cord and the most descending fibers have not yet terminated on their targets, while the sacral cords are mostly gray matter. In addition the spinal cord has two enlargements, the cervical enlargement and the lumosacral enlargement that give rise to the nerve plexuses for the arms and legs. The spinal cord has more gray matter at the cervical and lumbosacral levels than at the thoracic levels particularly in the ventral horns where lower motor neurons for the arms and legs reside.

B. Dorsal Column of the Spinal Cord

Furthermore, the present application is directed to stimulation of fibers within the dorsal column of the spinal cord and not the dorsal roots of the spinal cord according to some representative embodiments. Based upon the below description, one of skill in the art understands the fiber types that would need to be stimulated to produce the desired effect.

The dorsal column of the spinal cord contains four different fiber types that are classified according to axon diameter, for example A-α or I has a diameter of 13-20 μm, A-β or II has a diameter of 6-12 μm, A-δ or III has a diameter of 1-5 μm and C or IV has a diameter of 0.2-1.5 μm. Fibers A-α relay proprioception. Fibers A-β relay proprioception, touch (e.g., superficial touch, deep touch), and vibration. Fibers A-δ relay pain and temperature (cool). Fibers C relay temperature (warm) and itch.

The dorsal column or posterior column of the spinal cord is associated with the somatosensory pathways that is divided into to two pathways: the posterior column-medial lemniscal system that conveys proprioception, vibration sense, and fine and discriminative touch and the anterolateral systems that conveys pain, temperature sense and crude touch.

1. Posterior Column-Medial Lemniscal Pathway

The large-diameter, myelinated axons of the posterior column-medial lemniscal system conveys proprioception, vibration sense, and fine and discriminative touch. These axons enter the spinal cord via the medial portion of the dorsal root entry zone and ascend to the posterior column nuclei in the medulla.

Somatotopic organization of the dorsal column reveals fibers that are added laterally from higher levels as the dorsal columns ascend. As shown in FIG. 3, the medial portion of the dorsal column is the gracile fascilculus 31 and carries information from the legs and lower trunk while the more lateral portion of the dorsal column, cuneate fasciculus 32, carries information from the upper trunk above about T6 and from the arms and neck. First-order sensory neurons that have axons in the gracile and cuneate fasciculi synapse onto second-order neurons in the nucleus gracilis and nucleus cuneatus, respectively, which decussate as internal arcuate fibers and then form the medial lemniscus on the other side of the medulla. Next, the medial lemniscus axons terminate or synapse in the ventral posterior lateral nucleus (VPL) of the thalamus which project through the posterior limb of the internal capsule in the thalamic somatosensory radiations to reach the primary somatosensory cortex.

2. Spinothalamic Tract and Other Anterolateral Pathways

This part of the somatosensory system contains smaller-diameter and unmyelinated axons that carry or relay information about pain and temperature sense. The axons also enter the spinal cord via the dorsal root entry zone, however, they synapse in the gray matter of the spinal cord, mainly the dorsal horn marginal zone (lamina I) and/or lamina V. The second-order sensory neurons in the central gray matter cross over in the spinal cord anterior (ventral) commissure to ascend into the anterolateral white matter. Somatotopic organization reveals that the feet are most laterally represented fibers are added medially as the anterolateral pathways ascend the spinal cord. Eventually, the information is relayed in the thalamus which projects to the somatosensory cortex.

III. Stimulation Leads and Systems

Figure 5A:
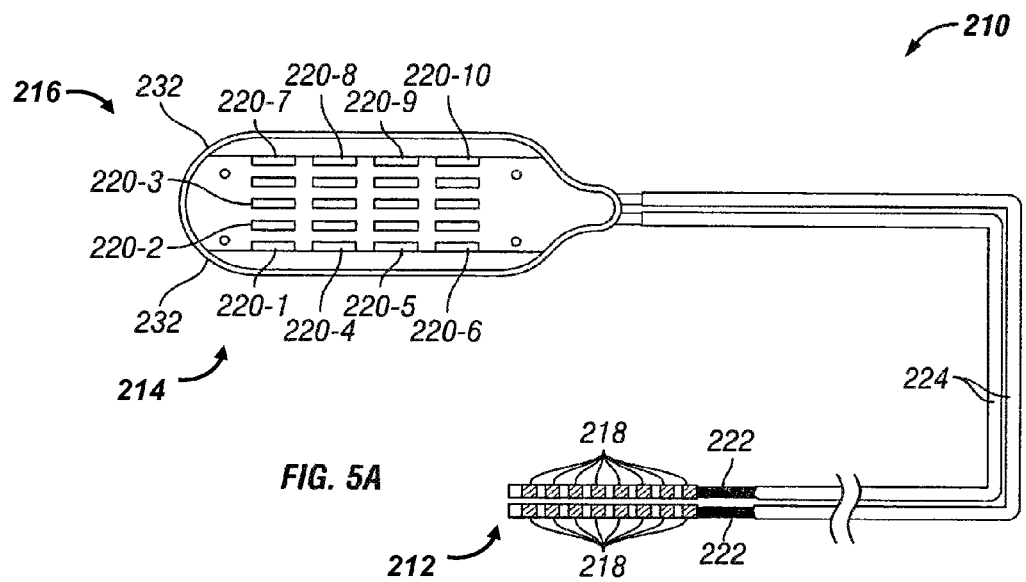
FIGS. 5A and 5B respectively depict a planar view and a cross-sectional view of a multi-column, multi-row paddle lead usable according to representative embodiments.

FIG. 5A depicts an example laminotomy lead 210 for treatment of multi-location pain locations according to one representative embodiment. Laminotomy lead 210 includes proximal end 212 and distal end 214. Proximal end 212 includes a plurality of electrically conductive terminals 218. Distal end 214 includes a plurality of electrically conductive electrodes 220 (only electrodes 220-1 through 220-10 are annotated for the sake of clarity) arranged within a flat, thin paddle-like structure 216. The electrodes 220 are mutually separated by insulative material of the paddle. For a paddle adapted for implantation within a cervical vertebral level, the electrodes are preferably spaced 1.5 mm laterally and 2.5 mm longitudinally. For a paddle adapted for implantation within a thoracic vertebral level, the electrodes are preferably spaced by 1.0 mm laterally and 2 mm or 3 mm longitudinally. Conductors 222 (which are embedded within the insulative material of the lead body) electrically connect electrodes 220 to terminals 218.

Figure 7:
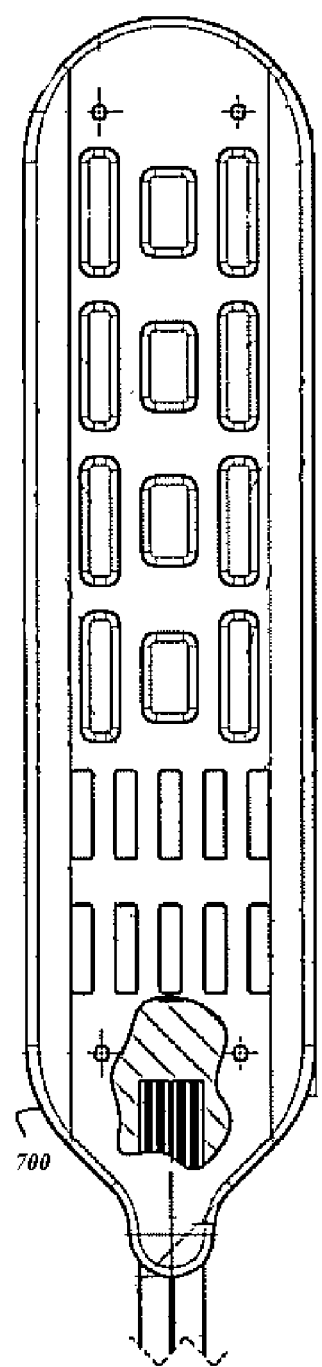
FIG. 7 depicts a stimulation paddle according to another representative embodiment.

In the specific example shown in FIG. 5A, paddle 216 includes five columns and four rows of electrodes 220. Alternative numbers of columns and rows may be employed. For example, in some embodiments, thirty-two or more electrodes are distributed into multiple rows and multiple columns. Also, every row need not contain the same number of columns. For example, a number of rows can include a "tripole" design having three columns of electrodes while additional rows can include five or more columns of electrodes to enable a greater amount of electrical field resolution (see paddle 700 as shown in FIG. 7). The multiple columns of electrodes enable lateral control of the applied electrical field to stimulate the exact lateral position of the pertinent nerve fiber(s). Specifically, it is desirable to selectively stimulate a given dorsal column fiber that is associated with an afflicted region of the patient's body without affecting regions of the patient's body. The multiple columns of paddles according to representative embodiments provide sufficient resolution to relatively finely control the stimulation of one or several specific fibers. Additionally, the multiple columns provide a degree of positional tolerance during the surgical placement of paddle 216 within the epidural space, because any one of the columns can be used to stimulate the pertinent nerve fiber(s). Also, if paddle 216 is displaced relative to the pertinent nerve fibers subsequent to implantation (e.g., due to lead migration), the stimulation pattern applied by the pulse generator can be shifted between columns to compensate for the displacement.

The multiple rows of paddles according to representative embodiments enable multiple pain locations to be treated with a single implanted lead. Specifically, a first row can be used to treat a first pain complaint (e.g., pain in the lower extremities) and a second row can be used to treat a second pain location (e.g., post-laminectomy pain in the back). Furthermore, by separating the first and second rows by one or several "buffer" rows of high-impedance electrodes, the stimulation in first and second rows may occur in a substantially independent basis. Specifically, anodes on the second row will have relatively minimal effect on the field distribution generated by cathodes on the first row.

In some embodiments, a paddle lead can be implanted within a patient such that the electrodes are positioned within the cervical or thoracic spinal levels. After implantation, an electrode combination on a first row of electrodes can be determined that is effective for a first pain location with minimal effects on other regions of the body. The first pain location can be addressed by stimulating a specific dorsal column fiber due to the relatively fine electrical field resolution achievable by the multiple columns. Then, another electrode combination on a second row of electrodes can be determined for a second pain location with minimal effects on other regions of the body. The second pain location could be addressed by stimulating another dorsal column fiber as an example. After the determination of the appropriate electrodes for stimulation, the patient's IPG can be programmed to deliver pulses using the first and second rows according to the determined electrode combinations.

When determining the appropriate electrode configurations, the selection of electrodes to function as anodes can often facilitate isolation of the applied electrical field to desired fibers and other neural structures. Specifically, the selection of an electrode to function as an anode at a position adjacent to another electrode functioning as a cathode causes the resulting electron/ion flow to be limited to tissues immediately surrounding the two electrodes. By alternating through the possible anode/cathode combinations, it is possible to gain greater resolution in the stimulation of dorsal column fibers. Also, it is possible to confine the applied electrical field to or away from the periphery of the paddle structure.

The operation of anodes can also be used to hyperpolarize neural tissue. Depending on the anode amplitude and the proximity to the pertinent neural tissue, the hyperpolarization can be used to prevent selected neural tissue from propagating action potentials. The hyperpolarization can also be used to prevent an adjacent cathode from initiating propagation of an action potential beginning at the selected neural tissue.

The multiple columns of electrodes also enable lateral "steering" of the electrical field using a single channel pulse generator. A single channel pulse generator refers to a pulse generator that provides an equal magnitude pulse to each active electrode at a given time. Specifically, each electrode is either "active" (i.e., it is coupled to the pulse generator output during pulse generation by a suitable gate or switch) or "inactive" (i.e., the gate or switch does not couple the electrode to the pulse generator output). Each "active" electrode experiences the same amplitude; only the polarity varies depending upon whether the electrodes are set as cathodes or anodes as defined by the positions of the respective gates or switches.

The steering of the electrical field occurs by selecting appropriate states for the electrodes. Depending upon the desired neural tissue to be stimulated, it may be beneficial to confine the electrical field along the periphery of paddle 216. Confinement of the electrical field along the periphery can be accomplished by setting electrode 220-1 to function as a cathode and setting electrode 220-2 to function as an anode. Because the electrical field will generally be confined between these two electrodes during stimulation pulses, only nerve fibers within the adjacent area will be stimulated. Generally speaking, nerve fibers past electrode 220-2 would not be stimulated when a pulse is delivered via electrode 220-1 due to the anodal blocking. If desired due to paddle placement or otherwise, an initial "inward" adjustment in the electrical field can be accomplished by setting electrode 220-1 as a cathode, setting electrode 220-2 as an anode, and setting electrode 220-3 as an anode thereby steering the stimulation toward the inward lateral direction. Another inward adjustment could be made by setting electrode 220-1 to the cathode state, setting electrode 220-2 to the high impedance state, and setting electrode 220-3 to the anode state.

The anodal blocking may be programmed to work in similar manner to controllably steer the stimulation toward the outward lateral direction and guard tissues at the periphery of the paddle 216. For example, electrode 220-3 can be set to function as a cathode and electrodes 220-2 and/or 220-1 can be set to the anodal state.

Figure 5B:
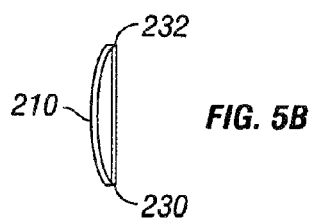
Figure 5C:
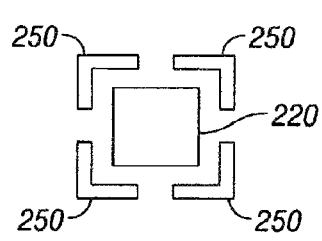
FIGS. 5C and 5D depict main electrodes with encircling and interstitial electrodes designs that could be employed within the paddle of FIGS. 5A and 5B.
Figure 5D:
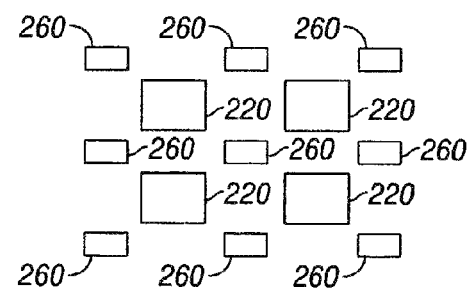

Other anode/cathode combinations and designs may be employed according to some representative embodiments. For example, as shown in FIG. 5C, each main electrode 220 of paddle structure 216 can be associated with one or several smaller encircling electrodes 250. The encircling electrodes 250 can be set as anodes to confine the electrical field during pulse generation substantially within the perimeter defined by the encircling electrodes 250. When employing such a design, other adjacent main electrodes 220 could be selectively set as anodes to stretch the field in a specific direction beyond the perimeter of the respective encircling electrodes 250, if desired. In some embodiments, since each encircling electrode 250 is intended to function as an anode, each encircling electrode 250 can be coupled to the same conductor 222 to minimize the number of conductors 222 within the lead 210. FIG. 5D depicts another design in which main electrodes 220 are associated with interstitial electrodes 260 for anodal blocking. In a similar manner, interstitial electrodes 250 could be coupled to a common conductor.

Conductors 222 are carried in sheaths 224. In some embodiments, each sheath 224 carries eight conductors 222. With only two sheaths 224 with eight conductors each, there would only be sixteen conductors 222. To accommodate the lower number of conductors 222 than electrodes 220, multiple electrodes 220 are coupled to the same conductor 222 (and, hence, to a common terminal 218). In one embodiment, electrodes 220-1 and 220-4 are coupled to a common conductor 222, electrodes 220-5 and 220-6 are coupled to a common conductor 222, electrodes 220-7 and 220-8 are coupled to a common conductor, and electrodes 220-9 and 220-10 are coupled to a common conductor.

In some embodiments, other electrode designs can be employed to minimize the number of conductors 222 required to support the various electrodes 220. For example, a relatively large number of electrodes (e.g., thirty-two, sixty-four, and greater) could be utilized on the paddle structure. The electrodes could be coupled to one or several electrical gates (e.g., as deposited on a flex circuit). The electrical gates can be controllably configured to couple each electrode to a conductor 222 carrying cathode pulses, to couple each electrode to an anode termination, or to maintain each electrode at a high impedance state. The electrical gates could be controlled using a main controller (a logic circuit) on the paddle structure that is coupled to a data line conductor 222. The data line conductor 222 is used to communicate signals from the IPG that identify the desired electrode states. The main controller responds to the signals by setting the states of the electrical gates as appropriate.

In another embodiment, a cathode conductor line 222 and an anode conductor line 222 are provided in one or several lead bodies along with a plurality of optical fibers. The optical fibers are used to carry optical control signals that control the electrode states. Specifically, the paddle structure includes photodetectors (e.g., photodiodes) that gate connections to the anode conductor line and the cathode conductor line. The use of optical fibers to carry optical control signals is advantageous, because the diameter of optical fibers suitable for such functionality is smaller than electrical conductors. Therefore, a larger number of electrodes (as compared to using a separate electrical conductor for each electrode) can be independently controlled while maintaining the lead body diameters at an acceptable size.

Terminals 218 and electrodes 220 are preferably formed of a non-corrosive, highly conductive material. Examples of such material include stainless steel, MP35N, platinum, and platinum alloys. In a preferred embodiment, terminals 218 and electrodes 220 are formed of a platinum-iridium alloy. Each conductor 222 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, a preferred embodiment uses conductors 222 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of representative embodiments, such insulative material protects the individual conductors 222 if its respective sheath 224 was breached during use.

In addition to providing the requisite strength, flexibility, and resistance to fatigue, conductors 222 formed of multi-strands of drawn-filled tubes, in accordance with the above description, provide a low resistance alternative to other materials. Specifically, a stranded wire, or even a coiled wire, of approximately 60 cm and formed of MP35N or stainless steel or the like would have a measured resistance in excess of 30 ohms In contrast, for the same length, a wire formed of multi-strands of drawn-filled tubes could have a resistance less than 4 ohms.

Sheaths 224 and paddle structure 216 are preferably formed from a medical grade, substantially inert material, for example, polyurethane, silicone, or the like. Importantly, such material should be non-reactive to the environment of the human body, provide a flexible and durable (i.e., fatigue resistant) exterior structure for the components of lead 210, and insulate adjacent terminals 218 and/or electrodes 220. Additional structure (e.g., a nylon mesh, a fiberglass substrate) (not shown) can be internalized within the paddle structure 216 to increase its overall rigidity and/or to cause the paddle structure 216 to assume a prescribed cross-sectional form.

The paddle structure may be fabricated to possess a substantially flat profile. As one alternative, the paddle structure may be fabricated to possess a prescribed arc along a transverse or lateral direction of the paddle structure 216 as shown in the cross-sectional view of FIG. 5B. On each longitudinal side of paddle structure 216, "wing" structures 232 may be formed for the purpose of retaining paddle structure 216 within the central portion of the epidural space. In some embodiments, one or several electrodes 220 could be disposed on the wing structures 232.

While a number of material and construction options have been discussed above, it should be noted that neither the materials selected nor a construction methodology is critical to the present invention.

Figure 6:
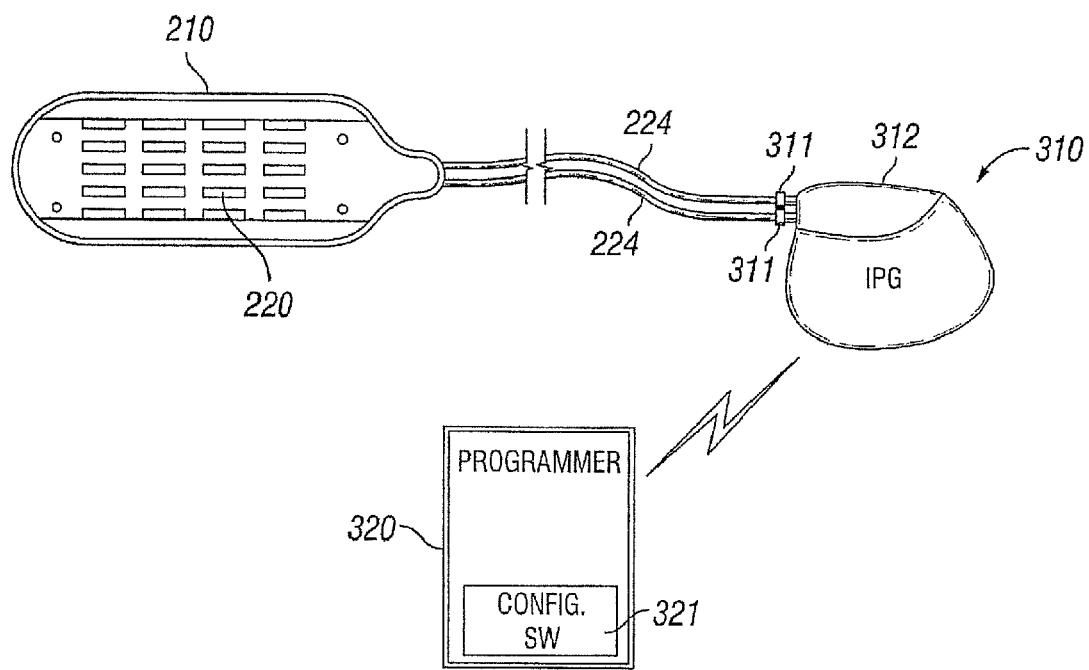
FIG. 6 depicts a system for implantable pulse generator with a multi-column, multi-row paddle lead in communication with a wireless programming device according to one representative embodiment.

FIG. 6 depicts paddle lead 210 coupled to IPG 310 which is in wireless communication with programmer device 320. An example of a commercially available IPG is the Eon™ Rechargeable IPG manufactured by Advanced Neuromodulation Systems, Inc, although any suitable IPG, such as RF powered devices, could be alternatively employed. As shown in FIG. 6, paddle lead 210 is coupled to the headers ports 311 of IPG 310. Each header port 311 electrically couples the respective terminals 218 (shown previously in FIG. 5A) to a switch matrix (not shown) within IPG 310.

The switch matrix selectively connects the pulse generating circuitry (not shown) of IPG 310 to the various terminals 218, and, hence to the electrodes 220. The sealed portion 312 of IPG 310 contains the pulse generating circuitry, communication circuitry, control circuitry, and battery (not shown) within an enclosure to protect the components after implantation within a patient. The control circuitry may comprise a microprocessor, one or more ASICs, and/or any suitable circuitry for controlling the pulse generating circuitry. The control circuitry controls the pulse generating circuitry to apply electrical pulses to the patient via electrodes 220 of paddle 210 according to multiple pulse parameters (e.g., pulse amplitude, pulse width, pulse frequency, etc.). The electrodes 220 are set to function as cathodes or anodes or set to a high-impedance state for a given pulse according to the couplings provided by the switch matrix. The electrode states may be changed between pulses.

When paddle lead 210 is initially implanted within the patient, a determination of the set(s) of pulse parameters and the electrode configuration(s) that effectively treat the patient's condition is made. The determination or programming typically occurs through a physician's interaction with configuration software 321 executed on the programmer device 320. Configuration software 321 steps the physician through a number of parameters and electrode configurations. In preferred embodiments, the electrode configurations are stepped through by laterally "steering" the electrical field by moving the anodes and/or cathodes along a row of the paddle as discussed above. The patient provides feedback to the physician regarding the perceived stimulation that occurs in response the pulse parameters and electrode configuration(s).

The physician effects changes to the parameters and electrode configuration(s) until optimal pulse parameters and electrode configuration(s) are determined The final pulse parameters and configurations are stored within IPG 310 for subsequent use. The pulse parameters and configurations are used by IPG 310 to control the electrical stimulation provided to the patient via paddle lead 310.

Although single channel IPGs have been described according to some embodiments, multiple current or voltage source IPGs could alternatively be employed. For example, a design similar to the stimulator disclosed in U.S. Pat. No. 5,501,703, which is incorporated herein by reference in its entirety, could be employed when coupled to a suitable paddle lead. The stimulation amplitudes associated with the various channels can be varied and delivered to adjacent electrodes to "steer" the stimulation. The steering of the stimulation field may be used to facilitate stimulation of the particular dorsal column fiber to address pain in a particular region of the patient's body while avoiding affecting other regions.

III. Stimulation of Nerve Fibers to Treat Pain

The stimulation system according to representative embodiments is utilized to preferentially stimulate nerve fibers in the dorsal column of the spinal cord. One technique that offers the ability to affect neuronal function is the delivery of electrical stimulation to target tissues via an implanted device having a probe. The probe is, for example, a stimulation lead or electrode assembly. An electrode assembly may be one electrode, multiple electrodes, or an array of electrodes in or around the target area. The proximal end of the probe is coupled to the system to operate the device to stimulate the target site. Thus, the probe is coupled to an electrical signal source, which, in turn, is operated to stimulate the predetermined treatment site of the dorsal column. Stimulation of the predetermined site is performed to modulate neuronal fibers of the dorsal column. Modulation of this neuronal tissue may result in efficacious treatment of a neurological disorder, for example, pain, in a subject. While optimal results from the treatment may result in the complete cessation of pain in a subject, any lessening of the amplitude of a subject's pain may be considered successful according to the representative embodiments.

Electrical energy can be delivered through electrodes positioned external to the dura layer surrounding the spinal cord. Stimulation on the surface of the cord (subdurally) is also contemplated; for example, stimulation may be applied to the dorsal columns as well as to the dorsal root entry zone or the dorsal root ganglia and/or nerve root. In preferred embodiments, the dorsal column of the spinal cord is stimulated; more particularly, any neuronal tissue of the dorsal column associated with any of the cervical vertebral segments (C1, C2, C3, C4, C5, C6, C7) and/or any tissue associated with any of the thoracic vertebral segments (T1, T2, T3, T4, T5, T6, T7, T8, T9, T10, T11, 12) and/or any tissue associated with any of the lumbar vertebral segments (L1, L2, L3, L4, L5, L6) and/or any tissue associated with the sacral vertebral segments (S1, S2, S3, S4, S5). Such electrical energy is provided by the laminotomy leads discussed above.

In certain embodiments, the stimulation device is used to stimulate fiber types of the dorsal column, more specifically in the area of the mid-thoracic and low-thoracic vertebral levels (T8-T11) or the high cervical levels (C1-C2). The advantage of high cervical stimulation of the dorsal column is that the white matter of the dorsal column is thickest in the cervical levels because this is where most of the ascending fibers have already entered the cord and most descending fibers have not yet terminated. Thus, stimulation of these fibers may result in a greater effect than stimulating the thoracic areas. Also, stimulation in this cervical area of the dorsal column may also elicit a sympathetic response in the peripheral nervous system.

The laminotomy lead of representative embodiments is implanted such that it stimulates the dorsal column of the spinal cord, more specifically, it stimulates a predetermined fiber type of the dorsal column. For example, the pain modulation may be altered by stimulating non-pain fibers, such as A-β fibers. More specifically, the periaqueductal gray receives inputs from the hypothalamus, amygdala, and cortex, and inhibits pain transmission in the dorsal horn via a relay in the rostral ventral medulla.

Representative embodiments are particularly useful in the treatment of pain in humans. Pain can include chronic pain, for example CRSII or CRSI. However, one skilled in the art appreciates that representative embodiments are applicable to other animals which experience pain. This may include, for example, primates, canines, felines, horses, elephants, dolphins, etc. Utilizing the various embodiments of the present invention, one skilled in the art may be able to modulate the pain via dorsal column stimulation to achieve a desirable result.

Thus, using the therapeutic stimulation system of the representative embodiments, the predetermined site is stimulated in an effective amount or effective treatment regimen to decrease, reduce, modulate or abrogate the pain. Thus, a subject is administered a therapeutically effective stimulation so that the subject has an improvement in the parameters relating to pain. The improvement is any observable or measurable improvement. Thus, one of skill in the art realizes that a treatment may improve the patient condition, but may not be a complete cure of the disease.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective. The improvement is any observable or measurable improvement. Thus, one of skill in the art realizes that a treatment may improve the patient condition, but may not be a complete cure of the disease.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of treating chronic pain in a patient with spinal cord stimulation, wherein (i) the chronic pain includes a first pain component within a first bodily sub-region of the trunk of the patient, (ii) the chronic pain includes a second pain component within a second bodily sub-region of the lower extremities of the patient separated from the first bodily sub-region by intervening bodily sub-regions, (iii) a stimulation lead is implanted within the epidural space of the patient, the method comprising:

selecting from the stimulation lead a first set of stimulation parameters including one or more first active electrode to treat chronic pain in the first bodily sub-region;

selecting from the stimulation lead a second set of stimulation parameters including one or more second active electrode to treat chronic pain in the second bodily sub-region;

wherein the stimulation lead comprises a paddle structure with at least 10 electrodes disposed in at least five mutually adjacent columns and at least two adjacent rows on the paddle structure;

controlling a pulse generator to apply electrical pulses to the patient through the stimulation lead according to the first and second set of stimulation parameters, wherein:

(i) a first electrical field, created by stimulation pulses having the first set of stimulation parameters applied through the first active electrode, has a restricted spatial resolution to stimulate a first set of one or more dorsal column fibers;

(ii) a second electrical field, created by stimulation pulses having the second set of stimulation parameters applied through the second active electrode, has a restricted spatial resolution to stimulate a second set of one or more dorsal column fibers;

wherein, in response to the applied electrical pulses, the patient experiences paresthesia in the first and second bodily sub-regions and the patient experiences minimal sensory effects from the applied electrical pulses in the intervening bodily sub-regions.

2. The method of claim 1 wherein the first set of one or more dorsal column fibers are associated with a first fasciculus of the dorsal column of the patient and the electrical field created by the stimulation pulses restricts the stimulation to the first set of dorsal column fibers associated with the first fasciculus while minimizing stimulation to adjacent dorsal column fibers in the first fasciculus or adjacent dorsal column fibers in another immediately adjacent fasciculus.

3. The method of claim 2 wherein the second set of one or more dorsal column fibers are associated with a second fasciculus of the dorsal column of the patient and the electrical field created by the stimulation pulses restricts the stimulation to the second set of dorsal column fibers associated with the second fasciculus while minimizing stimulation to adjacent dorsal column fibers in the second fasciculus or adjacent dorsal column fibers in another immediately adjacent fasciculus.

4. The method of claim 3 wherein the first fasciculus and the second fasciculus are the same.

5. The method of claim 4 wherein the first fasciculus and the second fasciculus are different.

6. The method of claim 1 wherein the paddle structure is implanted in a lower thoracic vertebral level selected from the group consisting of T8, T9, T10, T11 and T12.

7. The method of claim 1 wherein the paddle structure spans the physiological midline of the patient.

* * * * *